United States Patent [19]
Buxton

[11] Patent Number: 5,646,037
[45] Date of Patent: Jul. 8, 1997

[54] YEAST VECTORS

[75] Inventor: Frank Buxton, Muttenz, Switzerland

[73] Assignee: Ciba-Geigy Corporation, Tarrytown, N.Y.

[21] Appl. No.: 333,894

[22] Filed: Nov. 2, 1994

Related U.S. Application Data

[63] Continuation of Ser. No. 80,650, Jun. 21, 1993, abandoned, which is a continuation of Ser. No. 839,642, Feb. 21, 1992, abandoned.

[30] Foreign Application Priority Data

Feb. 25, 1991 [EP] European Pat. Off. ............ 91810124

[51] Int. Cl.$^6$ ................ C12N 1/15; C12N 1/21; C12N 15/81
[52] U.S. Cl. ................ 435/252.33; 435/254.21; 435/320.1
[58] Field of Search ............... 435/69.1, 172.1, 435/172.3, 252.33, 256, 320.1, 254.21

[56] References Cited

U.S. PATENT DOCUMENTS 4,760,022  7/1988  Molin et al. .................. 435/320.1

FOREIGN PATENT DOCUMENTS

| 0073635 | 3/1983 | European Pat. Off. . |
| 0340170 | 11/1989 | European Pat. Off. . |
| 0341215 | 11/1989 | European Pat. Off. . |
| WO88/08027 | 10/1988 | WIPO . |

OTHER PUBLICATIONS

Hinnen et al., *Current Topics in Microbiology and Immunology*, 96:101–117 (1982).
Futcher, *Yeast*, 4:27–40 (1988).
Hartley et al., *Nature*, 286:860–865 (1980).
Jordan et al., 15th Int. Conf. on Yeast Genetics and Molecular Biology 1990, Abstr. No. S436.
Umlauf et al., *EMBO J.*, 7:1845–1852 (1988).
Volkert et al., *Microbiological Reviews*, 53:299–317 (1989).
Bachmair et al., *Monatshefte fur Chemie*, 115:1229–1235 (1984).
Derwent Abstract 86–115946/18.
Lee et al., *Biotechnol. Bioeng.*, 31:783–789 (1988).
Bruschi, *Plasmid*, 17:78 (1987).
Feng et al., *Proc. Natl., Sci. Counc. B. ROC*, 10:175–183 (1986).
Broach, *Methods Enzymol.*, 101:307–325 (1983).
Bijvoet et al., 15th Int. Conf. on Yeast Genetics and Molecular Biology 1990, Abstr. No. S434.
Schwartz et al., *Biotechnol. Bioeng.*, 32:733–740 (1988).
Bruschi, 13th Int. Conf. on Yeast Genetics and Molecular Biology 1988, Abstr. No. S44.

*Primary Examiner*—James S. Ketter
*Attorney, Agent, or Firm*—W. Murray Spruill; James Scott Elmer; Shawn P. Foley

[57]  ABSTRACT

The invention relates to the field of genetic engineering and provides novel hybrid vectors based on the yeast two micron plasmid. The novel hybrid vectors are stably maintained in the cell during proliferation and are useful for the expression of heterologous genes in yeast in large scale batch and particularly in continuous culture.

33 Claims, 2 Drawing Sheets

YEAST VECTORS

This application is a continuation, of application Ser. No. 08/080,650, filed Jun. 21, 1993 now abandoned, which is a continuation of application Ser. No. 07/839,642 filed Feb. 21, 1992, now abandoned.

The invention relates to the field of genetic engineering and provides novel hybrid vectors based on the yeast two micron plasmid. The novel hybrid vectors are stably maintained in the cell during proliferation and are useful for the expression of heterologous genes in yeast in large scale batch and particularly in continuous culture.

BACKGROUND OF THE INVENTION

Although in genetic engineering numerous polypeptide expression systems for prokaryotic or eukaryotic hosts are already known, there is a continuing need for novel systems which have advantages over the known systems.

Very widely used as hosts are the eukaryotic yeasts, e.g. *Saccharomyces cerevisiae*, for which different types of vectors exist. One type of vector are the integrating vectors which do not contain autonomously replicating sequences (ARS) and therefore, cannot be maintained extrachromosomally in the cell. This type of vector usually consists of yeast and bacterial DNA moieties. The vectors can integrate into the genome of a transformed yeast cell by homologous recombination. Despite the relatively high stability of the inserted DNA, these vectors have disadvantages as expression vectors for the production of recombinant proteins in yeast. The first disadvantage is the low transformation rate because a recombination event must occur in the transformed cell to produce a stable transformant. The second is that the copy number of the vector in the stably transformed cell is low.

Another type of vector is an extrachromosomally replicating vector. These vectors can be grouped into three categories:

The first group contains autonomously replicating sequences (ARS). These vectors are usually present in high copy numbers in the cell, however, they are often lost during cell division.

The second group are so-called CEN vectors which contain a DNA sequence acting as a centromer during cell division. These vectors, though very stable, are present only in a few copies in the cells.

The third group is derived from naturally occuring yeast plasmids, the two micron-like plasmids (for review see A. Hinnen and B. Meyhack, Current Topics in Microbiology and Immunology 96: 101–107, 1982, and B. Futcher, Yeast 4: 27–40, 1988).

Several different two micron-like plasmids have been described. These are the two micron plasmid of *S. cerevisiae*, plasmids pSB1 and pSB2 from *Zygosaccharomyces bailii*, plasmid pSR2 from *Z. rouxii*, pSB3 from *Z. bisporus*, pSM1 from *Z. fermentati*, and pKD1 from *Kluyveromyces drosophilarum*. All seven plasmids are high copy number, double stranded circular DNA plasmids with remarkable similar structures: They all have two large exact inverted repeats diametrically opposed; they are found in two equimolar, isomeric forms; they all encode a FLP recombinase; they have an origin of replication immediately adjacent to one of the inverted repeats; all of the plasmids have at least three open reading frames. However, despite the structural and geometrical similarities, the plasmids share very little homology in their DNA sequence and in the amino acid sequences of the protein products of their genes (Futcher, op. cit.).

The naturally occuring two micron-like plasmids combine two essential features which are prerequisites for the use as starting vector in the construction of hybrid expression vectors for yeast: They are high copy number plasmids and are stably maintained in the cells.

The two micron plasmid of *S. cerevisiae* is found in the nucleus of almost all *S. cerevisiae* strains when isolated from the environment. The copy number of the two micron plasmid of *S. cerevisiae* is about 50 to 60 per cell. The rate of spontaneous plasmid loss is about $10^{-4}$ per cell per generation in rapidly growing haploid cells. Therefore it is not lost from *S. cerevisiae* populations in the laboratory except under extreme conditions.

The entire two micron plasmid of *S. cerevisiae* is 6318 base pairs in length. It has been fully sequenced (Hartley, J. L. and Donelson, J. E., Nature 286: 860–865, 1980). The plasmid contains two perfect 599 base pairs long inverted repeats, almost exactly diametrically opposed. The plasmid is found in two equimolar forms, A and B, which differ in the relative orientation of the two unique regions. The plasmid flips from one form the the other because of intramolecular recombination between the inverted repeats. The A and B forms of the plasmid are functionally equivalent.

The two micron plasmid contains four open reading frames: FLP, REP1, REP2 and D. Open reading frame FLP is a gene for a specific recombinase that causes the flipping of the A and B forms by recombining the inverted repeats. REP1 and REP2 are both required in cis or trans for plasmid stability. The D reading frame also encodes a gene involved in plasmid stability. The two micron plasmid also contains important cis-acting sites, e.g. an origin of replication from which the replication is initiated only once per S phase is located near the boundary of one of the inverted repeats. Another cis-acting element called STB or REP3 is involved in the stable inheritance of the plasmid to the daughter cells at mitosis. It seems to be the site of action of REP1 and REP2. Third, near the centre of each inverted repeat a small "FLP recognition target" (FRT) site is located at which the FLP recombinase acts.

The advantages of the naturally occuring two micron-like plasmids of yeast, i.e. stability and high copy number, are in general lost after the insertion of DNA. For example, the insertion of gene constructions containing either the PGK1, ADH1 or CYC1 promoter into the *S. cerevisiae* two micron plasmid resulted in a 4- to 10-fold decrease of the copy number within the cells in comparison with the two micron plasmid (B. E. Jordan et al., 15th Int. Conf. on Yeast Genetics and Molecular Biology, Abstr. No. S436).

A lot of attempts have been made in order to prepare two micron-like plasmid derived hybrid expression vectors which are more stable than the known ones. The attempts focussed for example on the insertion of foreign genes into such regions of the *S. cerevisiae* two micron plasmid which seemed not essential for the maintenance and copy number control of the plasmid in the cell. Other attempts focussed on the avoidance of bacterial DNA inserts in the two micron plasmid derived expression vectors. For example, in the PCT patent application WO88/08027 two micron plasmid derivatives are described which spontaneously loose the bacterial DNA sequences in yeast cells.

In the method used in said PCT application, bacterial DNA which is required for the propagation and multiplication of the two micron derived expression vectors in bacterial host cells, is inserted between two directly inverted FRT sites. A third FRT site is located on the plasmid in indirect orientation. After transformation of a yeast cell, the DNA located between the two FRT sites in direct orientation is deleted due to a homologous recombination event and a two micron derived plasmid without bacterial sequences arises in the yeast cell. A two micron plasmid derived vector which looses part of its DNA due to homologous recombination between two directly orientatd FRT sites is called a "disintegration vector".

It is an object of the present invention to provide futher stable yeast expression plasmids which are derived from a two micron plasmid.

DESCRIPTION OF THE INVENTION

The Hybrid Vectors

The present invention concerns a derivative of a yeast two micron-like plasmid, preferentially of the S. cerevisiae two micron plasmid, in which two regions between invertedly repeated FRT sites of the circular form have approximately the same length.

Such a plasmid derivative may comprise only two invertedly repeated FRT sites or an additional, third FRT site. The former kind of plasmid is hereinafter called a "symmetric two micron-like hybrid vector". The latter kind of plasmid is hereinafter called "symmetric two micron-like disintegration vector" despite it is not a real symmetric plasmid but gives rise to a symmetric two micron-like hybrid vector in the yeast cell transformed therewith.

Both kinds of two micron-like plasmid derivatives are hybrid vectors composed of DNA of a two micron-like plasmid, preferentially the two micron plasmid of S. cerevisiae, a selectable marker gene for yeast, a gene homologous or preferentially heterologous to yeast which can be expressed under the control of a promoter functional in yeast, and optionally further DNA sequences of viral, prokaryotic or eukaryotic origin. These further DNA sequences can provide to the vector essential structural or functional features like, for example, a procaryotic or eukaryotic origin of replication, a selection marker gene, or restriction cleavage sites, or can also only have the function of filling up the two regions between the two invertedly repeated FRT sites of an unsymmetric two micron-like plasmid derivative or of an "unsymmetric" disintegration vector in order to construct a symmetric two micron-like hybrid vector or a symmetric disintegration vector.

A symmetric two micron-like hybrid vector of the invention does preferentially not contain bacterial DNA sequences, i.e. DNA derived from a bacterial genome, plasmid or virus. However, a two micron-like disintegration vector of the invention may comprise DNA sequences of prokaryotic origin between the two directly repeated FRT sites which are excised from the vector in the transformed yeast cell in which the symmetric two micron-like hybrid vector is generated from the disintegration vector. These DNA sequences comprise, for example, a bacterial origin of replication which allows multiplication and propagation of the vector in a suitable prokaryotic host and optionally a bacterial selection marker which allows selection of a transformed prokaryote. DNA sequences allowing multiplication and optionally such allowing selection of plasmids in any prokaryotic host known in the field of genetic engineering can be applied, however such allowing multiplication and selection in E. coli are the most commonly used.

Naturally occuring two micron-like plasmids have a high copy number in the fungal cell, and consist of double stranded circular DNA with remarkable similarities in their structures: They all have two large exact inverted repeats diametrically opposed; they are found in two equimolar, isomeric forms; they all encode a FLP recombinase; and they have an origin of replication immediatedely adjacent to one of the inverted repeats. Different naturally occuring two micron-like plasmids have been described which can all be used for the constructon of symmetric two micron-like hybrid or disintegration vectors of the invention. Two micron-like plasmids which can be used for the preparation of the vectors of the invention are preferentially the plasmids pSB1 and pSB2 from Zygosaccharomyces bailii, plasmid pSR2 from Z. rouxii, pSB3 from Z. bisporus, pSM1 from Z. fermentati, and pKD1 from Kluyveromyces drosophilarum and most preferentially the two micron plasmid of S. cerevisiae itself. All plasmids are described in B. Futcher, Yeast 4: 27–40, 1988. Because it is to be expected that further two micron-like plasmids exist, the invention concerns also symmetric or disintegration vectors derived from further two micron-like plasmids.

In a two micron-like hybrid vector which is symmetric within the meaning of the present invention or in a disintegration vector which gives rise to such a symmetric two micron-like hybrid vector the lengths of the regions located between the two invertedly repeated FRT sites have a ratio from about 1:1 up to about 5:4, i.e. the larger region is up to about 20% larger than the smaller one. Preferred is a plasmid in which the larger region is up to about 15%, more preferentially about up to 10%, most preferentially up to about 5% larger than the smaller region.

Heterologous structural genes which can be part of a symmetric two micron-like vector or disintegration vector of the invention originate from viruses, prokaryotic cells or eukaryotic cells and may be derived from genomic DNA or from cDNA prepared via the mRNA route or may be synthesized chemically, and are coding for a wide variety of useful polypeptides, including glycosylated polypeptides, in particular of higher eukaryotic origin, especially of mammalian, such as animal or preferentially human origin. Useful proteins are, for example, enzymes which can be used, for the production of nutrients and for performing enzymatic reactions in chemistry, or polypeptides which are useful and valuable as nutrients or for the treatment of human or animal diseases or for the prevention thereof, for example hormones, polypeptides with immunomodulatory, anti-viral and anti-tumor properties, antibodies, viral antigens, vaccines, clotting factors, foodstuffs and the like.

Such heterologous structural genes are for example those coding for hormones such as secretin, thymosin, relaxin, calcitonin, luteinizing hormone, parathyroid hormone, adrenocorticotropin, melanoycte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFα or TGFβ, e.g. TGFβ1, β2 or β3, growth hormone, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, proteinase inhibitors such as $α_1$-antitrypsin, SLPI and the like, hepatitis virus antigens, such as hepatitis B virus surface or core antigen or hepatitis A virus antigen, or hepatitis nonA-nonB antigen, plasminogen activators, such as tissue plasminogen activator or urokinase, tumour necrosis factor, somatostatin, renin, β-endorphin, immunoglobulins, such as the light and/or heavy chains of immunoglobulin D, E or G, or humanmouse hybrid immunoglobulins, immunoglobulin binding factors, such as immunoglobulin E binding factor, e.g. sCD23 and the like, calcitonin, human calcitonin-related peptide, blood clotting factors, such as factor IX or VIIIc, erythropoietin, eglin, such as eglin C, hirudin, desulfatohirudin, such as desulfatohirudin variant HV1, HV2 or PA, human superoxide dismutase, viral thymidin kinase, β-lactamase, glucose isomerase. Preferred genes are those coding for a human α-interferon or hybrid interferon, particularly hybrid interferon BDBB, human tissue plasminogen activator (t-PA), hepatitis B virus surface antigen (HBVsAg), insulin-like growth factor I and II, eglin C and most preferentially desulfatohirudin, e.g. variant HV1.

Preferred symmetric plasmids of the invention are pFBY12, pFBY12R, pFBY13, pFBY13R, pFBY13rev, pFBY13revR Preferred disintegration vectors of the invention are pFBY27, pFBY27R, pFBY27rev, pFBY27revR, pFBY66, pFBY66R, pFBY98, pFBY98R, pFBY99, and pFBY99R.

Preparation of the Hybrid Vectors

The invention also concerns a method for the preparation of a hybrid vector of the invention. Both the symmetric two micron-like hybrid vectors and disintegration vectors of the invention can be prepared using conventional chemical or biological in vitro synthesis procedures, the latter is for example the conventional polymerase chain reaction method. However, preferentially the vectors are constructed and prepared using recombinant DNA techniques.

For the preparation by recombinant DNA techniques suitable DNA fragments can be ligated in vitro in conventional manner in order to construct a symmetric two micron-like hybrid vector or a disintegration vector of the invention. The ligation mixture is then transformed into a suitable prokaryotic or eukaryotic host depending on the nature of the regulatory elements used, and a transformant containing the desired vector is selected according to conventional procedures. The vectors can be multiplicated by means of the transformed hosts and can be isolated in conventional manner. The choice of the host depends on the regulatory sequences located on the vector.

In case a disintegration vector is constructed, the host may not be a yeast cell if the formation of a symmetric vector is not desired. A disintegration vector of the invention preferentially comprises regulatory sequences functional in prokaryotes, e.g. E. coli, and accordingly a prokaryotic host, e.g. E. coli is preferred for the construction and multiplication of the vector.

The preparation of a symmetric two micron-like hybrid vector plasmid can be performed either directly, i.e. the final vector is constructed by ligating suitable DNA fragments, transformation of a suitable host and isolating it from the transformed host. In this case the choice of the host depends, as above, from the regulatory DNA sequences located on the vector. Preferred hosts are eukaryotic hosts, most preferentially yeast cells, because a symmetric vector of the invention does preferentially not contain bacterial DNA sequences. Another possibility is to prepare the symmetric vectors of the invention starting from a disintegration vector.

For this preparation yeast cells are transformed with a disintegration vector of the invention which contains two pairs of invertedly and one pair of directly repeated FRT sites. The DNA embraced by the pair of directly orientated FRT sites is lost spontaneously in a transformed yeast cell. Thus, the transformed yeast cell forms in vivo a symmetric two micron-like hybrid vector if a disintegration vector is used in which both the DNA regions embraced by the two invertedly oriented pairs of FRT sites have approximately the same length, i.e. the ratio of their lengths is as defined above for the symmetric two micron-like vectors.

Transformed Hosts and Preparation Thereof

The invention also concerns hosts transformed with the hybrid vectors of the invention. Such hosts can be used for the propagation and multiplication of the plasmids. Non-yeast eukaryotic hosts and preferentially bacterial hosts, for example E. coli, can be used for the propagation of the disintegration vectors. Bacterial hosts are used if the disintegration vector comprises bacterial regulating DNA sequences and optionally bacterial selectable markers between the two directly repeated FRT sites. Transformed yeast cells can be used for propagating symmetric two micron-like hybrid vectors, preferentially for such which do not comprise bacterial DNA sequences. If a derivative of the two micron plasmid of S. cerevisiae is used, the transformed yeast host is preferentially a S. cerevisiae strain.

Preferred transformed hosts are E. coli strains transformed with either of the preferred disintegration vectors described hereinbefore. Preferred are also S. cerevisiae strains transformed with either of the symmetric two micron-like hybrid vectors or with either of the preferred disintegration vectors described hereinbefore. In the latter case, the transformed yeast cells carry the symmetric plasmids developped from the disintegration vectors by recombination after the transformation.

The invention also concerns a method for the preparation of transformed hosts by conventional methods using a symmetric two micron-like hybrid vectors or disintegration vectors of the invention. Said method comprises the steps of (a) transforming a suitable host and (b) culturing the transformed hosts in nutrient medium optionally in the presence of selection conditions.

Transformed hosts of the invention can also be used for the production of protein products the genes of which are located on a symmetric two micron-like hybrid vector. In this case, the host is preferentially a yeast, most preferably a S. cerevisia strain, and the gene is under the control of regulatory sequences which are functional in yeast.

Preparation of Polypeptide Products

The invention also concerns a method for producing a yeast or non-yeast polypeptide comprising the steps of (a) culturing a yeast strain transformed with a symmetric two micron like hybrid vector containing an expression cassette consisting of a promoter functional in yeast, a signal sequence encoding a signal peptide functional in yeast, a structural gene coding for a yeast or non-yeast polypeptide, and optionally a terminator functional in yeast, (b) isolating said polypeptide The transformed yeast strains are cultured in a liquid medium containing assimilable sources of carbon and nitrogen and inorganic salts. Additionally, the nutrient medium may also contain growth promoting substances and/or substances exerting a selection pressure in order to positively select cells containing the hybrid plasmid. Growth promoting substances include, for example, trace elements such as iron, zinc, manganese and the like, or individual amino acids.

If the symmetric two micron plasmid contains a gene conferring resistance to an antibiotic substance, cells containing such hybrid plasmid will survive in a medium supplemented with the antibiotic substance whereas cells which have lost said hybrid plasmid will not. If the hybrid plasmid contains a gene providing for prototrophy in an auxotrophic yeast mutant, e.g. the URA3, LEU2 or HIS3 gene, a selection pressure can be exerted by omitting the respective gene product in the nutrient medium.

Any promoter which is suitable for the expression of proteins in yeast can be used for the construction of the said expression cassette. Included within the scope of the present invention are regulated yeast promoters such as MEL1, heat shock promoters, suc2, GAL1/CYC1, cup1, GAL1/10, ADHI and preferentially PHO5, as well as constitutive promoters such as GAPDH, PGK, PYK, PDC1 and preferentially GAPFL.

Depending on the promoter used in the expression cassette, inductive or derepressive conditions must be applied in order to allow the production of the recombinant gene product. For example, if the well known regulated yeast PHO5 promoter (see, for example, European Patent No. 0 100 561) is used, the content of inorganis phosphate in the nutrient medium must be reduced in order to ensure maximum levels of mRNA transcripts and, consequently, maximum yields of proteins.

The cultivation is carried out employing conventional techniques, either in a batch culture or in continuous culture. The culturing conditions such as temperature, pH of the medium and fermentation time are selected in such way that maximal levels of polypeptides are produced. A chosen yeast swain is, for example, grown under aerobic conditions in submerged culture with shaking or stirring at a temperature of about 25° C. to 35° C., preferably at about 30° C. In the case the polypeptide is secreted from the producing cell due to the use of a signal sequence in the construction of the expression cassette, the product is isolated from the culture supernatant. If the polypeptide is secreted not into the supernatant but into the periplasmic space of the cell, the cells are to be treated with chemical agents or enzymes removing the cell wall. If the product is not secreted, the cells are harvested and the polypeptides are liberated from the cell interior according to conventional methods.

The polypeptides obtainable according to the present invention and the preferred embodiments thereof are the products of the genes and the preferred genes, respectively, which were already defined hereinbefore as useful for the construction of the expression hybrid vectors of the invention.

Most preferred is the production of hirudin or IGF-I by means of a symmetric two micron like hybrid vector, preferably derived from the S. cerevisiae two micron plasmid, containing the hirudin or IGF-I gene operably linked with the GAPDH promoter and α-factor signal sequence and terminator.

EXAMPLES

Figure 1A:
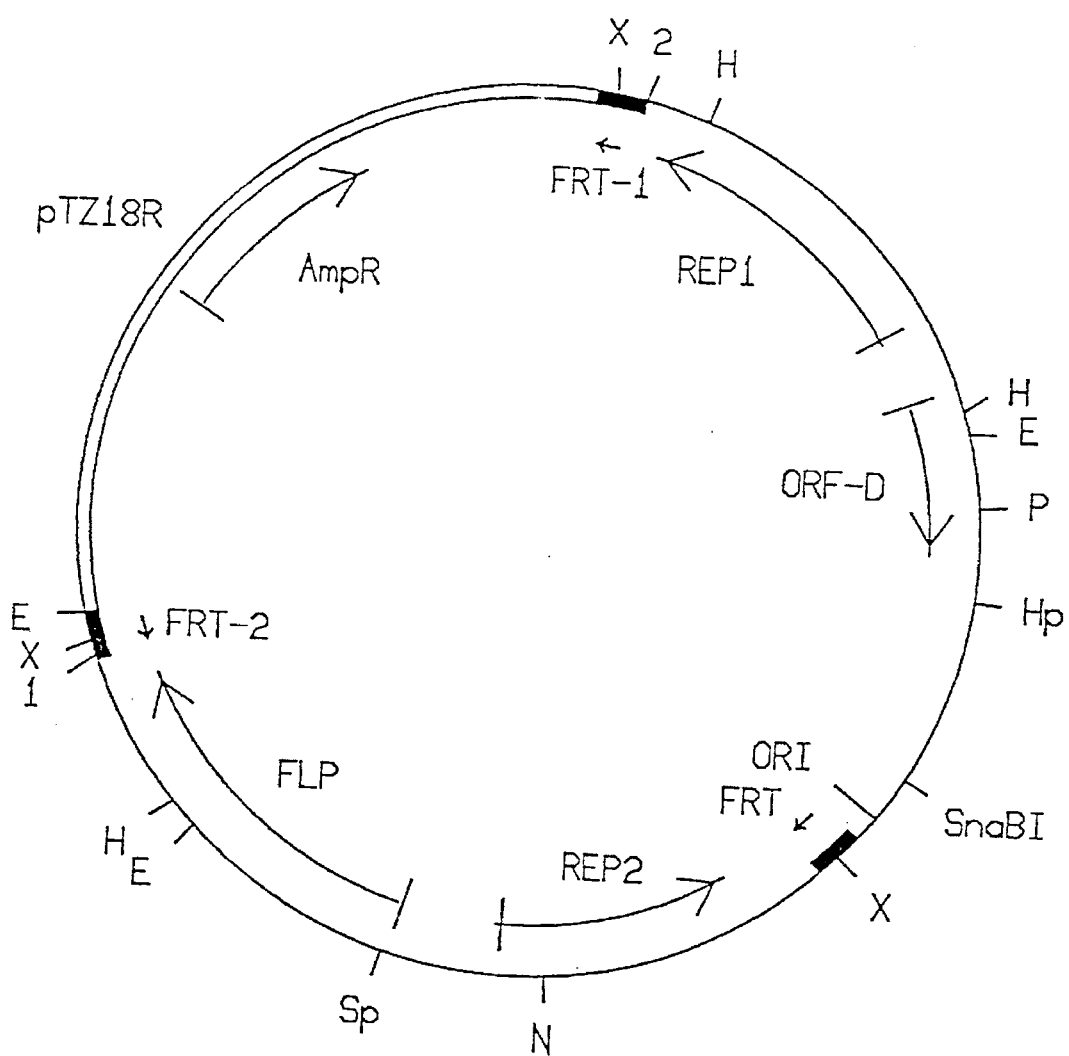
FIG. 1A is a physical map of the disintegration plasmid pFBY2. It consists of all of the two micron DNA (single line) integrated into pTZ18R (double line) in such a way as to duplicate the FRT sites (FRT-1 and FRT-2) as direct repeats separating the bacterial and S. cerevisiae derived DNA. The long arrows indicate open reading frames, the little arrows indicate the orientation of the FRT repeats and "ORI" indicates the S. cerevisiae origin of replication. E=EcoRI, H=HindIII, Hp=HpaI, N=NcoI, P=PstI, S=SphI, X=XbaI.

The following examples illustrate the invention without being meant to be limitative.

| Buffer, Media | |
|---|---|
| LGT | Low gelling temperature agarose |
| TAE | 40 mM Tris(hydroxymethyl)aminomethane; 2 mM Ethylenediaminetetraacetic acid (disodium salt) Acetic acid to pH 7.6 |
| YPD | 20 g Bactopeptone; 10 g Yeast extract; 20 g Glucose per liter $H_2O$ |
| YNB | 6.7 g Bacto yeast Nitrogen base without amino acids; 20 g Glucose per liter $H_2O$ |
| 2YT | 16 g Tryptone; 10 g Yeast extract; 10 g NaCl per liter $H_2O$ |
| Xgal | 0.05 mg/ml 5-bromo-4-chloro-3-indolyl-B-D-galactopyranoside |
| IPTG | 0.05 mM Isopropyl-B-D-thiogalactopyranoside |
| Ampicillin | 25 mg/l final concentration in media |
| CA buffer | 20 mM Tris(hydroxymethyl)aminomethane; 7 mM $MgCl_2$; 5 mM dithiothreitol; 100 mm KCl; HCl to pH 7.5 |
| H buffer | 50 mM Tris(hydroxymethyl)aminomethane; 10 mM $MgCl_2$; 1 mM dithiothreitol; 100 mM NaCl; HCl to pH 7.5 |
| ligase buffer | 20 mM Tris(hydroxymethyl)aminomethane; 10 mM $MgCl_2$; 10 mM dithiothreitol; HCl to pH 7.5 |
| BAP buffer | 50 mM Tris(hydroxymethyl)aminomethane; 50 mM NaCl; HCl to pH 8.0 |
| S1 buffer | 100 mM NaCl; 50 mM $CH_3COONa$; 0.1 mM $ZnCl_2$; acetic acid to pH 4.5 |
| T4 buffer | 67 mM Tris(hydroxymethyl)aminomethane; 6.7 mM $MgCl_2$; 17 mM $(NH_4)_2SO_4$; 5 mM dithiothreitol; HCl to pH 8. |
| LSB | 20 mM Tris(hydroxymethyl)aminomethane; 1 mM Ethylenediaminetetraacetic acid (disodium salt); 200 mM NaCl; HCl to pH 7.5 |
| HSB | 20 mM Tris(hydroxymethyl)aminomethane; 1 mM Ethylenediaminetetraacetic acid (disodium salt); 1M NaCl; HCl to pH 7.5 |

| Buffer, Media | |
| --- | --- |
| TE | 10 mM Tris(hydroxymethyl)aminomethane, 1 mM EDTA, pH 8 |
| HIN buffer | 7 mM Tris(hydroxymethyl)aminomethane, 7 mM MgCl$_2$, 50 mM NaCl, HCl ad pH 7.5 |

Strains and Plasmids

*E. coli* DH5αF': *Escherichia coli* K12 F' endA1 hsdR17(r⁻ m⁺) supE44 thi1 recA1 pyrA relA1 PHI80lacZdelM15 del(lacZYA-argF)U169 Hanahan D (1983) Studies on transformation of *Escherichia coli* with plasmids. J Mol Biol 166: 557 (Bethesda Research Laboratories)

Plasmid pTZ18R: Plasmid derived from pUC18 includes an M13 origin of replication so it can become single stranded and be packaged in M13 phage heads with the aid of a helper M13 phage. Mead DA, Szczesna-Skorupa E, Kemper B (1986) Single stranded DNA 'blue' T7 promoter plasmids: a versatile tandem promoter system for cloning and protein engineering. Protein Engineering 1: 67–74. (Pharmacia).

Phage M13KO7: Helper M13 phage carrying kanamycin resistance. Mead DA, Szczesna-Skorupa E, Kemper B (1986) Single stranded DNA 'blue' T7 promoter plasmids: a versatile tandem promoter system for cloning and protein engineering. Protein Engineering 1: 67–74. (Pharmacia).

*S. cerevisiae* H449: *Saccharomyces cerevisiae* MATα; ura3del5; leu2-3; leu2-112; prb1; cps1; [cir]o Feb. 18, 1988, DSM 4413.

*S. cerevisiae* AB110: *Saccharomyces cerevisiae* X *S. carlsbergensis* MATα; ura3-52; his4-580; leu2; pep4-3; [cir°] Schuster JR, Moyer DL, Lee H, Dennis A, Smith B, Merryweather JP (1989) Yeast mutants conferring resistance to toxic effects of cloned human insulin-like growth factor I. Gene 83: 47–55. Deposited as ATCC 20709 on May 9, 1984 at the American Type Culture Collection.

Plasmid pFBY2: This plasmid is constructed by inserting the 166 bp AluI fragment containing the FRT site from *S. cerevisiae* two micron plasmid between the HindIII and EcoRI sites of pTZ18R and the whole of the two micron plasmid cut with XbaI into the unique XbaI site of pTZ18R. The pFBY2 plasmid, which forms the basis of most of the plasmids constructed in the examples hereinafter, thus contains the whole of pTZ18R and the whole of two micron plasmid plus a third copy of the FRT site. The pieces of DNA are assembled so that recombination between the two directly repeated FRT sites leads to the regeneration of a two micron A-form circle and a plasmid consisting of pTZ18R plus one FRT site. The latter is lost in yeast cells. A physical map of this disintegration vector is given in FIG. 1. pFBY2 is deposited as DSM6271.

Plasmid pFBY4: This plasmid consists of a 1.1 kb XbaI fragment containing the whole of the URA3 gene of *S. cerevisiae* cloned into the unique XbaI site of pTZ18R. This plasmid serves as a convenient source for a 1.1 kb URA containing XbaI fragment. pFBY4 is deposited as DSM 6272.

Plasmid pFBY5:pFBY5 is derived from a large plasmid containing the whole of the *S. cerevisiae* two micron plasmid plus the URA3 and Leu2 genes of *S. cerevisiae* in the bacterial vector pUC18. Into the unique SalI site of this vector is inserted a 1.1 kbp SalI fragment containing an expression cassette consisting of a promoter derived from the *S. cerevisiae* GAPDH gene fused to the PHO5 signal sequence which in turn is fused to a synthetic hirudin encoding DNA fragment, which is followed by the PHO5 terminator. pFBY 5 is deposited as DSM 6273.

Plasmid pFBY7:pFBY7 consists of pFBY4 cut with BamHI and KpnI ligated to a BamHI/KpnI fragment of *S. cerevisiae* DNA that contains the CDC9 gene. This plasmid serves as a source of a 3.9 kbp HindIII/KpnI fragment that contains both URA3 and CDC9 in a head to tail orientation. It is deposited as DSM 6274.

Plasmid pFBY29: This plasmid consists of a 2 kbp BamHI/SalI fragment containing the LEU2 gene. The fragment is inserted between the BamHI and SalI sites of pTZ18R. pFBY29 serves as a source of a 2.0 kbp fragment containing LEU2. It is deposited as DSM 6275.

Plasmid pFBY65: This plasmid has a convenient 1.4 kbp SmaI fragment which contains the GAPDH promoter fused to the a-factor signal and leader sequences, which in turn are fused to a synthetic IGF-I gene followed by the α-factor terminator. It is deposited as DSM 6276.

GENERAL METHODS

Purification of Restriction Fragments by ElutipD (Schmitt JJ, Cohen BN (1983) Quantitative isolation of restriction fragments from low-melting agarose by Elutip-d affinity chromatography. Analyt Biochem 133: 462–464)

The digested DNA is electrophoresed through a LGT agarose gel using TAE buffer, with Ethidium bromide (0.2 mg/l) in the gel and buffer. The DNA is visualised with long wave UV and the bands cut out. A photographic record, if required is made now. The slice is place in a 10 ml polypropylene tube to which is added sufficient LSB to reduce the agarose concentration to less than 0.2%. The agarose is melted by incubating at 65° C. for 30 min, mixed well and then equilibrated at 37° C. for 30 min The chromatography is done at room temperature using a flow rate of 2 drops per second. A Schleicher and Schuell Elutip-d column is washed with 2.5 ml HSB and then with 2.5 ml LSB. The DNA solution at 37° C. is then passed through column. The column is rinsed with 2.5 ml LSB and the DNA eluted with 0.4 ml HSB.

The DNA is ethanol precipitated by adding 1 ml ethanol and centrifuging at 15 000 rpm for 30 min. The supernatant is removed with a drawn out sterile glass pipette, carefully avoiding the pellet. The DNA pellet is washed by adding 500 µl 70% EtOH/water, centrifuging for 5 min and removing the supernatant as before. The DNA is dried for 2 min in a Speedvac and resupended in water.

Blunt Ending DNA with T4 Polymerase

To 1 pM of ends add 2 µl T4 buffer 10×, 2 µl dXTP (0.5 mM each of dG,dT,dC), 2 µl dATP 0.5 mM, 1U T4 polymerase, H$_2$O to 20 µd. Incubate at 37° C. for 30 min. (Definition: 1U T4 polymerase will incorporate 10 nM dXTP into DNA in 30 min at 37° C. when primed with 0.2 mM denatured *E.coli* DNA)

Alkaline Phosphatasing DNA 1 pM of ends, 5 µl 10xBAP buffer, water to give 50 µl final volume. Bacterial Alkaline phosphatase BAP (for 5' extensions use 500U from Bethesda Research Laboratories or 0.5U from International Biotechnologies; for blunt ends use twice as much). Incubate at 65° C. for 30 min and remove the BAP either by trebling with 10 µl of 1 mg/ml Proteinase K in TE for 37° C. for 30 min followed by phenol extraction, ether extraction and ethanol precipitation, or by separating the DNA from the protein by running the DNA on a LGT gel followed by ElutipD chromatography.

EXAMPLE 1

Construction of pFBY8 and pFBY8R

2 µg of pFBY7 is cleaved to completion by HindIII anf KpnI in CA buffer. These fragments are separated on a 0.8% LGT gel in TAE buffer. The 3.9 kbp fragment is cut out and the DNA is purified by ElutipD chromatography. The DNA fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

2 µg of pFBY2 is cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 9.3 kbp band is cut out and the DNA is purified by ElutipD chromatography. The DNA fragment is blunt ended with 1 unit of T4 polymerase as above.

Approximately 20 ng of the insert is ligated to 20 ng of each of the vectors in separate ligation reactions in the presence of 1 mM ATP and ligation buffer by 0.5 units of T4 ligase for 3 h at room temperature.

These ligation mixtures are used to transform 40 µl aliquots of competent *E. coli* DH5αF' cells and plated on 2YT plates containing ampicillin, Xgal and IPTG. After 16 h incubation at 37° C., white colonies are picked and miniscreened using EcoRI and PstI to confirm the presence of the correct insert and orientation.

pFBY8 and pFBY8R differ in the orientation of the URA3 CDC9 insert. In pFBY8 the insert is inserted in the way that the direction of transcription of the URA3 gene is opposite to that of the ampR gene.

These vectors are examples for disintegration vectors giving rise to asymmetric plasmids in a transformed *S. cerevisiae* cell.

EXAMPLE 2

Construction of pFBY11 and pFBY11P

Seven 1 µg aliquots of pFBY2 are digested with either 0, 1, 0.5 or 0.25, 0.125, 0.0625, or 0.03125 units of XbaI for 1 hour in CA buffer at 37° C. The enzyme reaction is stopped by the addition of 10 mM EDTA and the fragments separated on a 0.8% LGT gel. At one of the enzyme concentrations the linearised plasmid is clearly separated from the other fragments so this is cut out and purified by ElutipD chromatography. The DNA fragment is treated with 100 units of S1 nuclease in S1 buffer at room temperature for 30 min. This is inactivated by heating at 65° C. for 10 min and then the ends are properly blunt ended with 1 unit T4 polymerase in the presence of 0.05 mM each of dATP, dCTP, dGTP and dTTP for 30 min at 37° C. The enzyme is heat inactivated at 65° C. for 10 min.

Approximately 20 ng of each of this prepared fragment is ligated in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., white colonies are picked and miniscreened using HindIII to confirm the presence of the correct plasmid and PstI XbaI double digests to determine the deletion of the correct XbaI site.

This gives rise to three possible plasmids. Two of them are selected and named pFBY11 and pFBY11P. They differ in which of the two FRT direct repeats are inactivated. In pFBY11 the first FRT site upstream and in pFBY11P the first FRT site downstream of the ampR gene is destroyed.

EXAMPLE 3

Construction of pFBY12 Family

Figure 1B:
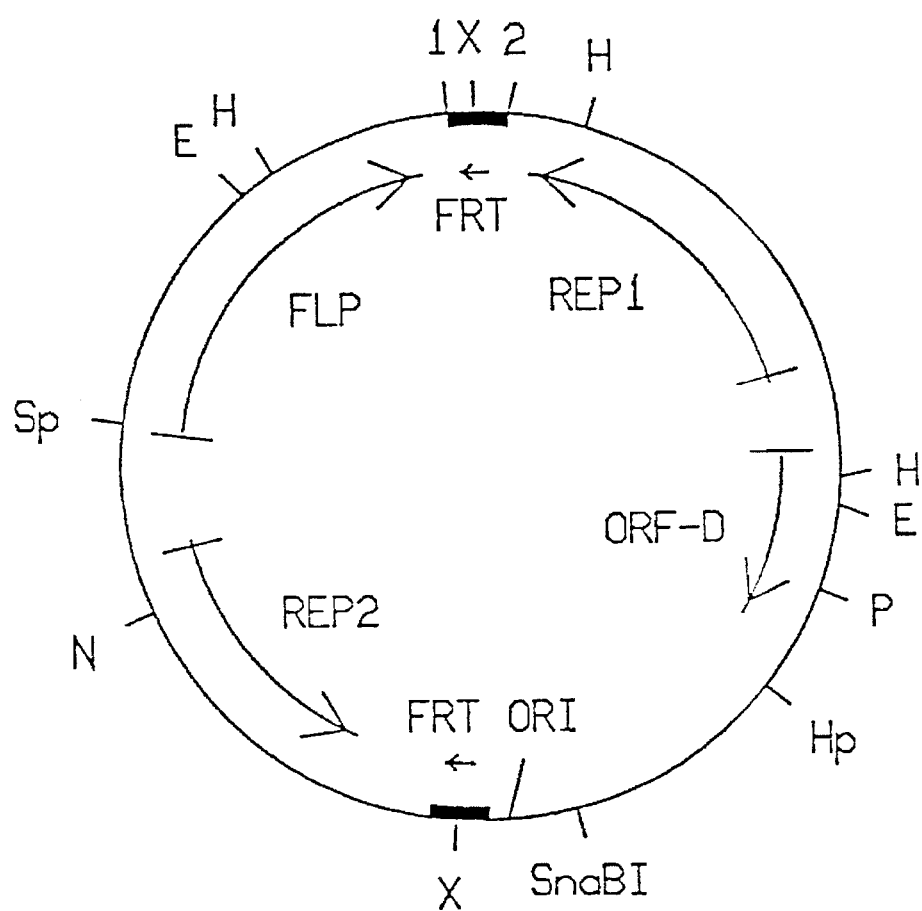
FIG. 1B shows the plasmid yielding from in vitro or in vivo recombination between the FRT sites FRT-1 and FRT-2 of the disintegration plasmid pFBY2. In S. cerevisiae the plasmid B exists in two forms, one as shown in the figure and one that is a simple inversion, by recombination between the indirectly repeated FRT sites. Signs and symbols as in FIG. 1A.

In the pFBY12 and the pFBY13 families of plasmids, the latter is described in Example 4, inserts of various genes are made in the SnaBI site of pFBY2, thus enlarging the size of the rightmost FRT bounded fragment depicted in FIG. 1A. In the P series, e.g. pFBY12P, pFBY13Prev etc. the XbaI site in the middle of the FRT-1 repeat shown in FIG. 1A is deleted thus these plasmids are much more assymetric than the corresponding plasmids that have the FRT-2 site inactivated by a deletion of this XbaI site. It is evident from the results given hereinafter, that the P series of plasmids are uniformaly less stable than their otherwise identical but symmetric plasmids.

2 µg of pFBY7 is cleaved to completion by HindIII anf KpnI in CA buffer. These fragments are separated on a 0.8% LGT gel in TAE buffer. The 3.9 kbp fragment is cut out and the DNA is purified by ElutipD chromatography. The DNA fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

Two separate vectors are prepared from pFBY11 and pFBY11P. Two µg of each are cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 9.3 kbp band is cut out and the DNA is purified by ElutipD chromatography. The DNA fragment is blunt ended with 1 unit of T4 polymerase as above.

Approximately 20 ng of the insert is ligated to 20 ng of each of the vectors in separate ligation reactions in the presence of 1 mM ATP and ligation buffer by 0.5 units of T4 ligase for 3 h at room temperature.

These ligation mixtures are used to transform 40 µl aliquots of competent *E. coli* DH5αF' cells and plated on 2YT plates containing ampicillin, Xgal and IPTG. After 16 h incubation at 37° C., whites colonies are picked and miniscreened using EcoRI and PstI to confirm the presence of the correct insert and orientation.

This gives rise to 4 plasmids. pFBY12 and pFBY12R from pFBY11 that differ in the orientation of the URA3 CDC9 insert and two, pFBY12P and pFBY12PR, that likewise differ, from pFBY11P. In pFBY12R and pFBY12PR the direction of transcription of the URA3 gene is the same as of the ampR gene.

pFBY12 and pFBY12P have competely identical sequence, except for the deletions in the FRT sites (these are sequenced and are shown to be <30 bp). This difference means that pFBY12 is a symmetric plasmid and pFBY12P is not. pFBY12R and pFBY12PR differ in an identical manner to pFBY12 and pFBY12P.

13

EXAMPLE 4

Construction of pFBY13 Family of Plasmids

Following the scheme below it is possible to construct 8 plasmids from the four pFBY12 plasmids that contain GAPFLyHIR in both orientations.

2 μg of each of the plasmids of the pFBY12 family is cleaved to completion by SalI. The 5' phosphate groups are removed with 500 units of BAP in BAP buffer at 65° C. for 30 min to prevent self ligation of the vector. These fragments are separated on a 0.8% LGT gel in TAE buffer. The 13.2 kbp band is cut out and the DNA is purified by ElutipD chromatography.

2 μg of pFBY5 is cleaved to completion by SalI in H buffer. These fragments are separated on a 0.8% LGT gel in TAE buffer. The 1.1 kbp fragment carrying the GAPFLyHIR gene is cut out and the DNA is purified by ElutipD chromatography.

Approximately 20 ng of the 1.1 kbp insert is ligated to 20 ng of each of the vectors of the pFBY12 family in reactions containing 1 mM ATP and ligation buffer by 0.5 units of T4 ligase for 3 h at room temperature.

These ligation mixtures are used to transform 40 μl aliquots of competent E. coli DH5αF' cells and plated on 2YT plates containing ampicillin, Xgal and IPTG. After 16 h incubation at 37° C., white colonies are picked and miniscreened using SalI and PstI to confirm the presence of the correct insert and orientation.

pFBY12 gave rise to pFBY13 and pFBY13R. pFBY12R gave rise to pFBY13rev and pFBY13revR. pFBY12P gave rise to pFBY13P and pFBY13PR. pFBY12PR gave rise to pFBY 13Prev and pFBY 13PrevR.

pFBY13, pFBY13rev, pFBY13P and pFBY13Prev carry the GAPFLyHIR gene in the same transcriptional orientation as URA3, whereas in pFBY13R, pFBY13revR, pFBY13PR and pFBY13PrevR these two genes are orientated in opposite direction.

Like the pFBY12 series, the pFBY13 series of plasmids contains again pairs of plasmids that differ solely in which FRT site is deleted. Thus pFBY13P is a less symmetric version of pFBY13. Likewise, also the other plasmids indicated with "P" are less symmetric than, but otherwise identical to their respective counterparts.

EXAMPLE 5

Construction of pFBY23

2 μg of pFBY2 is cleaved to completion by FspI in CA buffer. The restriction endonuclease is inactivated by heating at 65° C. for 10 min. The volume is doubled by the addition of water and the DNA fragments are blunt ended with 1 unit of T4 polymerase in the presence of 0.05 mM each of dATP, dCTP, dGTP and dTTP for 30 min at 37° C. The enzyme is heat inactivated at 65° C. for 10 min. After ethanol precipitation the DNA is recut with HindIII and EcoRI. These fragments are separated on a 2% LGT gel in TAE buffer. The 170 bp and the 523 bp fragments are cut out and the DNAs are purified by ElutipD chromatography.

2 μg of pTZ18R is cleaved to completion by EcoRI and HindIII in CA buffer. These fragments are separated on a 0.8% LGT gel in TAE buffer. The 2.8 kbp band is cut out and the DNA is purified by ElutipD chromatography.

Approximately 20 ng of each of the prepared fragments are ligated together with 10 pM of an unphosphorylated BamHI linker of the sequence GGGATCCC and 1 mM ATP and ligation buffer by 0.5 units of T4 ligase for 3 h at room temperature.

14

This ligation mixture is used to transform 40 μl of competent E. coli DH5αF' cells and plated on 2YT plates containing ampicillin, Xgal and IPTG. After 16 h incubation at 37° C., whites colonies are picked and miniscreened using EcoRI HindIII double digest to confirm the presence of the correct insert and a HindIII BamHI double digest to show the BamHI linker in the previous FspI site.

EXAMPLE 6

Construction of pFBY24

2 μg of pFBY23 is cleaved to completion by HindIII and EcoRI in CA buffer. Theses fragment are separated on a 0.8% LGT gel in TAE buffer. The 701 bp band is cut out and the DNA is purified by ElutipD chromatography.

2 μg of pFBY2 is cleaved to completion by HindIII and PstI in CA buffer. These fragments are separated on a 0.8% LGT gel in TAE buffer. The 3.8 kbp fragment is cut out and the DNA is purified by ElutipD chromatography.

2 μg of pFBY2 is cleaved to completion by PstI and XbaI in CA buffer. These fragments are separated on a 0.8% LGT gel in TAE buffer. The 1.95 kbp fragment is cut out and the DNA is purified by ElutipD chromatography.

2 μg of pFBY2 is cleaved to completion by XbaI and EcoRI in CA buffer. These fragments are separated on a 0.8% LGT gel in TAE buffer. The 2.9 kbp fragment is cut out and the DNA is purified by ElutipD chromatography.

Approximately 20 ng of each of the prepared fragments are ligated together in the presence of 1 mM ATP and ligation buffer by 0.5 units of T4 ligase for 3 h at room temperature.

This ligation mixture is used to transform 40 μl of competent E. coli DH5αF' cells and plated on 2YT plates containing ampicillin, Xgal and IPTG. After 16 h incubation at 37° C., white colonies are picked and miniscreened using HindIII EcoRI and PstI XbaI double digests to confirm the presence of the correct inserts and BamHI to show the presence of the new BamHI site.

pFBY24 is identical to pFBY2 with the complete sequences of the plasmids pTZ18R and 2μ separated by directly repeated FRT sites, except for the insertion of a BamHI site into the FspI site at the 3' end of the FLP gene.

EXAMPLE 7

Construction of pFBY25 and pFBY25R

2 μg of pFBY4 is cleaved to completion by XbaI in CA buffer. Theses fragment are separated on a 0.8% LGT gel in TAE buffer. The 1.1 kbp band is cut out and the DNA is purified by ElutipD chromatography.

2 μg of pFBY24 is cleaved to completion by BamHI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 9.3 kbp band is cut out and the DNA is purified by ElutipD chromatography. The DNA fragment is blunt ended with 1 unit of T4 polymerase as above.

Approximately 20 ng of each of the prepared fragments are ligated together in the presence of 1 mM ATP and ligation buffer by 0.5 units of T4 ligase for 3 h at room temperature.

This ligation mixture is used to transform 40 μl of competent E. coli DH5αF' cells and plated on 2YT plates containing ampicillin, Xgal and IPTG. After 16 h incubation at 37° C., whites colonies are picked and miniscreened using BamHI to confirm the presence of the correct insert and EcoRI PstI double digest to determine the orientation.

This gives rise to two plasmid pFBY25 and pFBY25R. The only difference between these two plasmids is that in the former the URA3 gene has the same and in the latter the reverse orientation in comparison with the ampR gene.

EXAMPLE 8

Construction of pFBY27 and pFBY27R, and pFBY27rev and pFBY27revR

To create plasmids that could both loose the bacterial sequences and still remain symmetric, one of the FspI sites in pFBY2 is replaced with a BamHI linker. The location of this newly created BamHI site is in FIG. 1A marked "1". In plasmids such as pFBY27 and also pFBY79 described hereinafter, inserts are present at both the SnaBI site and the created BamHI so that when the plasmid recombines to remove the bacterial sequences a symmetric plasmid results.

2 µg of pFBY5 is cleaved to completion by SalI in H buffer. The fragments are separated on a 0.8% LGT gel in TAE buffer. The 1.1 kbp band is cut out and the DNA is purified by ElutipD chromatography. The fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

2 µg of pFBY25 and pFBY25R are cleaved seperately to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 10.5 kbp band is cut out and the DNA is purified by ElutipD chromatography.

Approximately 20 ng of the fragment prepared from pFBY5 are ligated to pFBY25 or pFBY25R in seperate reactions in the presence of 1 mM ATP and ligation buffer by 0.5 units of T4 ligase for 3 h at room temperature.

These ligation mixtures are used to transform 40 µl of competent E. coli DH5αF' cells and plated on 2YT plates containing ampicillin, Xgal and IPTG. After 16 h incubation at 37° C., whites colonies are picked and miniscreened using PstI and EcoRI digests to confirm the presence and orientation of the correct inserts.

This gives rise to two plasmids pFBY27 and pFBY27R from pFBY25. In both plasmids the URA3 gene has the same orientation as ampR. They only differ in the orientation of the hirudin expression cassette GAPFLyHIR, which is in pFBY27 oriented in the opposite and in pFBY27R in the same direction as URA3. The two plasmids pFBY27rev and pFBY27revR arise from pFBY25R. They also only differ in the orientation of the hirudin expression cassette which has in pFBY27rev the same and in pFBY27revR the opposite orientation compared to URA3, which is in the opposite orientation to ampR in both plasmids.

These four plasmids are disintegration vectors which, when transformed into S. cerevisiae, undergo an intramolecular recombination event to yield a symmetric plasmid containing the whole of the 2µ sequences, URA3 as selectable marker and a GAPDH-HIR expression cassette.

EXAMPLE 9

Construction of pFBY66 and pFBY66R

2 µg of pFBY65 is cleaved to completion by SmaI in CA buffer. These fragments are separated on a 0.8% LGT gel in TAE buffer. The 1.4 kbp band is cut out and the DNA is purified by ElutipD chromatography.

2 µg of pFBY25 is cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 10.5 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40.1 of competent E. coli DH5αF' cells and plated on 2YT plates containing ampicillin, Xgal and IPTG. After 16 h incubation at 37° C., whites colonies are picked and miniscreened using PstI and XbaI digests to confirm the presence and orientation of the correct inserts.

This gave rise to two plasmids pFBY66 and pFBY66R that differ only in the orientation of the IGF-I expression cassette. These two plasmids are disintegration vectors which when transformed into S. cerevisiae, recombine to yield a symmetric plasmid containing the whole of the 2µ sequences, URA3 as selectable marker and an expression cassette containing an IGF-I gene under the control of the GAPDH promoter

EXAMPLE 10

Construction of pFBY74

2 µg of pFBY29 is cleaved to completion by BamHI in CA buffer. These fragments are separated on a 0.8% LGT gel in TAE buffer. The 2.0 kbp band is cut out and the DNA is purified by ElutipD chromatography.

2 µg of pFBY24 is cleaved to completion by BamHI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 9.3 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent E. coli DH5αF' cells and plated on 2YT plates containing ampicillin, Xgal and IPTG. After 16 h incubation at 37° C., whites colonies are picked and miniscreened using BamHI and a SalI XbaI double digest to confirm the presence and orientation of the correct inserts. The LEU2 gene is in the same orientation as ampR of pFBY74.

EXAMPLE 11

Construction of pFBY78

2 µg of pFBY5 is cleaved to completion by SalI in H buffer. These fragments are separated on a 0.8% LGT gel in TAE buffer. The 1.1 kbp band is cut out and the DNA is purified by ElutipD chromatography.

Plasmid pFBY4Sp, which is a derivative of pFBY4 with the SphI site removed, is prepared by cleaving pFBY4 to completion with SphI, deleting the single stranded ends with $T_4$ DNA polymerase and religating.

2 µg of pFBY4Sp is cleaved to completion by SalI in H buffer. The 5' phosphate groups are removed with 500 units of BAP in BAP buffer at 65° C. for 30 min to prevent self ligation of the vector. This fragment is separated on a 0.8%

LGT gel in TAE buffer. The 3.9 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using SalI and PstI digests to confirm the presence and orientation of the correct inserts.

The URA3 and GAPFLyHIR genes are transcribed in the same direction as the ampR gene of pFBY78. pFBY78 contains URA3 and GAPFLyHIR on a conveniently excisable 2.3 kb HindIII/SacI fragment.

EXAMPLE 12

Construction of pFBY79

2 µg of pFBY78 is cleaved to completion by HindIII and SacI in CA buffer. These fragments are separated on a 0.8% LGT gel in TAE buffer. The 2.3 kbp band is cut out and the DNA is purified by ElutipD chromatography. The fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

2 µg of pFBY74 is cleaved to completion by SnaBI in CA buffer. The 5' phosphate groups are removed with 500 units of BAP in BAP buffer at 65° C. for 30 min to prevent self ligation of the vector. This fragment is separated on a 0.8% LGT gel in TAE buffer. The 11.3 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using BamHI and PstI digests to confirm the presence and orientation of the correct inserts.

pFBY79 is a disintegration vector that when transformed into *S. cerevisiae* yields, by recombination, asymmetric plasmid that contains LEU2 and URA3 as selectable markers and a GAPFLyHIR expression cassette. pFBY79 has the URA3 and GAPFLyHIR genes transcribed in the opposite direction to the ampR gene and LEU2 gene.

EXAMPLE 13

Construction of pFBY87

2 µg of pFBY2 is cleaved to completion by XbaI and PstI in CA buffer. These fragments are separated on a 0.8% LGT gel in TAE buffer. The 2.0 kbp band is cut out and the DNA is purified by ElutipD chromatography.

2 µg of pTZ18R is cleaved to completion by XbaI and PstI in CA buffer. These fragments are separated on a 0.8% LGT gel in TAE buffer. The 2.8 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using HindIII and a PstI XbaI double digest to confirm the presence of the correct inserts.

EXAMPLE 14

Construction of pFBY87Bg

2 µg of pFBY87 is cleaved to completion by XbaI and NsiI in CA buffer. These fragments are separated on a 0.8% LGT gel in TAE buffer. The 3.3 kbp band is cut out and the DNA is purified by ElutipD chromatography.

2 µg of pFBY87 is cleaved to completion by NsiI and HindIII in CA buffer. These fragments are separated on a 0.8% LGT gel in TAE buffer. The 1.2 kbp band is cut out and the DNA is purified by ElutipD chromatography.

2 µg of pFBY88RBg is cleaved to completion by XbaI and HindIII in CA buffer. These fragments are separated on a 2.0% LGT gel in TAE buffer. The 0.31 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using HindIII, BglII and a XbaI NsiI double digest to confirm the presence of the correct inserts.

EXAMPLE 15

Construction of pFBY88R

2 µg of pFBY24 is cleaved to completion by XbaI and HindIII in CA buffer. These fragments are separated on a 2.0% LGT gel in TAE buffer. The 0.31 kbp band is cut out and the DNA is purified by ElutipD chromatography.

2 µg of pTZ19R is cleaved to completion by XbaI and HindIII in CA buffer. These fragments are separated on a 0.8% LGT gel in TAE buffer. The 2.8 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using a HindIII XbaI double digest to confirm the presence of the correct inserts.

EXAMPLE 16

Construction of pFBY88RBg

A BglII site is engineered into plasmid pFBY88R by a modification of the in vitro mutagenesis technique of Kunkel (Proc Natl Acad Sci 82 (1985) 488–492)

The uracil containing template is prepared by transforming pFBY88R (10 ng) into BW313 (dut-ung-) and plating on 2xYT plates plus ampicillin. A single colony is picked into 10 ml of 2xYT containing uridine 50 ng/ml and ampicillin 25 µg/ml and grown at 37 C shaking for 4 h. 25 l of M13K07 (5×10^10 pfu/ml) are added and the culture incubated a further 1 h. After which 0.1 ml kanamycin (75 mg/m) is added and incubation continued overnight. Single stranded DNA is prepared from the supernatant in the usual manner for M13.

The mutagenic primer of the sequence shown under SEQ ID No. 1 is synthesised.

5 pM of this primer is phosphorylated by 0.5 units of T4 polynucleotide kinase in ligase buffer containing 1 mM ATP by incubating at 37° C. for 30 min. The enzyme is inactivated by incubation at 65° C. for 10 min.

0.5 pM of the U substituted template is hybridised with 5 pM of phosphorylated primer in Hin buffer by heating to 65 C for 2 min and allowing it to cool slowly to room temperature.

The T substituted strand is synthesised by incubating this hybridised DNA in the following mixture DTT 6 mM, dATP 0.05 mM, dCTP 0.05 mM, dTTP 0.05 mM, dGTP 0.05 mM, ATP 1 mM in a total volume of 50 µl HIN buffer with 1 unit Klenow and 1 unit T4 DNA ligase at 37 C for 30 min followed by 3 h at room temperature This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using a BglII HindIII double digest to confirm the presence of the correct mutation. The sequence of the whole of the HindIII XbaI fragment is determined from both strands using reverse and universal primers to rule out the appearance of other mutations in this region. A plasmid with the correct sequence is picked and called pFBY88RBg.

EXAMPLE 17

Construction of pFBY89 pFBY89 is similar to pFBY2 but a BglII site is introduced into the pFBY2 vector having the BamHI site introduced in position "1" shown in FIG. 1A (see Example 8) by in vitro mutagenesis at the right hand end of the FRT-1 site. The location of this site is indicated with "2" in FIG. 1A. This newly created site can also used in combination with the said BamHI site introduced at position "1" shown in FIG. 1A to create further symmetric two micron disintegration vectors.

2 µg of pFBY2 is cleaved to completion by XbaI and EcoRI in CA buffer. These fragments are separated on a 0.8% LGT gel in TAE buffer. The 2.9 kbp band is cut out and the DNA is purified by ElutipD chromatography.

2 µg of pFBY24 is cleaved to completion by EcoRI and BamHI in CA buffer. These fragments are separated on a 2.0% LGT gel in TAE buffer. The 0.18 kbp band is cut out and the DNA is purified by ElutipD chromatography.

2 µg of pFBY24 is cleaved to completion by BamHI and PstI in CA buffer. These fragments are separated on a 0.8% LGT gel in TAE buffer. The 4.3 kbp band is cut out and the DNA is purified by ElutipD chromatography.

2 µg of pFBY87Bg is cleaved to completion by PstI and XbaI in CA buffer. These fragments are separated on a 0.8% LGT gel in TAE buffer. The 4.3 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using BglII and EcoRI XbaI and BamHI PstI double digests to confirm the presence of the correct inserts.

pFBY89 is almost identical to pFBY2 with the complete sequences of pTZ18R and 2µ separated by directly repeated FRT sites, except that like pFBY24, pFBY89 has a BamHI site inserted into the FspI site at the 3' end of the FLP gene (position "1" in FIG. 1A). pFBY89 also has a BglII site inserted at the 3' end of the REPI gene (position "2" in FIG. 1A).

EXAMPLE 18

Construction of pFBY94 and pFBY94R

2 µg of pFBY89 is cleaved to completion by BglII in CA buffer. The 5' phosphate groups are removed with 500 units of BAP in BAP buffer at 65° C. for 30 min to prevent self ligation of the vector. These fragments are separated on a 0.8% LGT gel in TAE buffer. The 10.5 kbp band is cut out and the DNA is purified by ElutipD chromatography.

pFBY4Bam is constructed by removing the polylinker between the SalI and HindIII sites by digestion with these restriction enzymes, treating with $T_4$ DNA polymerase for creating blunt ends, and ligating the blunt ends together with a BamHI linker of the sequence GGGATCCC. This plasmid serves as source for a 1.1 kbp URA3 containing BamHI fragment.

2 µg of pFBY4Bam is cleaved to completion by BamHI in CA buffer. These fragments are separated on a 0.8% LGT gel in TAE buffer. The 1.1 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using PstI and a SmaI XbaI double digests to confirm the presence of the correct inserts. The URA3 gene is transcribed in the same direction as the ampR gene in pFBY94R and in the opposite direction to the ampR gene in pFBY94.

EXAMPLE 19

Construction of pFBY95 and pFBY95R

2 µg of pFBY89 is cleaved to completion by BamHI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 10.5 kbp band is cut out and the DNA is purified by ElutipD chromatography.

2 µg of pFBY4BAM is cleaved to completion by BamHI in CA buffer. These fragments are separated on a 0.8% LGT gel in TAE buffer. The 1.1 kbp band is cut out and the DNA is purified by ElutipD chromatography.

Approximately 20 ng of the prepared fragments are ligated together in the presence of 1 mM ATP and ligation buffer by 0.5 units of T4 ligase for 3 h at room temperature.

This ligation mixture is used to transform 40 µl of competent *E. coli* DH5αF' cells and plated on 2YT plates containing ampicillin, Xgal and IPTG. After 16 h incubation at 37° C., whites colonies are picked and miniscreened using PstI and BamHI digests to confirm the presence of the correct inserts. The URA3 gene is transcribed in the same direction as the ampR gene in pFBY95 and in the opposite orientation in pFBY95R.

EXAMPLE 20

Construction of pFBY96 and pFBY 96R

2 µg of pFBY94 is cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 11.6 kbp band is cut out and the DNA is purified by ElutipD chromatography.

2 μg of pFBY5 is cleaved to completion by SalI in H buffer. This fragment are separated on a 0.8% LGT gel in TAE buffer. The 1.1 kbp band is cut out and the DNA is purified by ElutipD chromatography. The fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

Approximately 20 ng of the prepared fragments are ligated together in the presence of 1 mM ATP and ligation buffer by 0.5 units of T4 ligase for 3 h at room temperature.

This ligation mixture is used to transform 40 μl of competent *E. coli* DH5αF' cells and plated on 2YT plates containing ampicillin, Xgal and IPTG. After 16 h incubation at 37° C., whites colonies are picked and miniscreened using PstI and EcoRI digests to confirm the presence of the correct inserts. The GAPFLyHIR expression cassette is transcribed in the opposite direction to ampR in pFBY96 and in the same direction as ampR in pFBY96R.

EXAMPLE 21

Construction of pFBY97 and pFBY 97R

2 μg of pFBY94R is cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 11.6 kbp band is cut out and the DNA is purified by ElutipD chromatography.

2 μg of pFBY5 is cleaved to completion by SalI in H buffer. This fragment are separated on a 0.8% LGT gel in TAE buffer. The 1.1 kbp band is cut out and the DNA is purified by ElutipD chromatography. The fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

Approximately 20 ng of the prepared fragments are ligated together in the presence of 1 mM ATP and ligation buffer by 0.5 units of T4 ligase for 3 h at room temperature.

This ligation mixture is used to transform 40 μl of competent *E. coli* DH5αF' cells and plated on 2YT plates containing ampicillin, Xgal and IPTG. After 16 h incubation at 37° C., whites colonies are picked and miniscreened using PstI and EcoRI digests to confirm the presence of the correct inserts. The GAPFLyHIR expression cassette is transcribed in the opposite direction to ampR in pFBY97 and in the same direction as ampR in pFBY97R.

EXAMPLE 22

Construction of pFBY98 and pFBY98R

2 μg of pFBY95 is cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 11.6 kbp band is cut out and the DNA is purified by ElutipD chromatography.

2 μg of pFBY5 is cleaved to completion by SalI in H buffer. This fragment are separated on a 0.8% LGT gel in TAE buffer. The 1.1 kbp band is cut out and the DNA is purified by ElutipD chromatography. The fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

Approximately 20 ng of the prepared fragments are ligated together in the presence of 1 mM ATP and ligation buffer by 0.5 units of T4 ligase for 3 h at room temperature.

This ligation mixture is used to transform 40 μl of competent *E. coli* DH5αF' cells and plated on 2YT plates containing ampicillin, Xgal and IPTG. After 16 h incubation at 37° C., whites colonies are picked and miniscreened using PstI and EcoRI digests to confirm the presence of the correct inserts. The GAPFLyHIR expression cassette is transcribed in the opposite direction to ampR in pFBY98 and in the same direction as ampR in pFBY98R.

EXAMPLE 23

Construction of pFBY99 and pFBY99R

2 μg of pFBY95R is cleaved to completion by SnaBI in CA buffer. The 5' phosphate groups are removed with 500 units of BAP in BAP buffer at 65° C. for 30 min to prevent self ligation of the vector. These fragments are separated on a 0.8% LGT gel in TAE buffer. The 11.6 kbp band is cut out and the DNA is purified by ElutipD chromatography.

2 μg of pFBY5 is cleaved to completion by SalI in H buffer. This fragment are separated on a 0.8% LGT gel in TAE buffer. The 1.1 kbp band is cut out and the DNA is purified by ElutipD chromatography. The fragment is blunt ended with 1 unit of T4 polymerase in the presence of 0.05 mM each of dATP, dCTP, dGTP and dTTP for 30 min at 37° C. The enzyme is heat inactivated at 65° C. for 10 min.

Approximately 20 ng of the prepared fragments are ligated together in the presence of 1 mM ATP and ligation buffer by 0.5 units of T4 ligase for 3 h at room temperature.

This ligation mixture is used to transform 40 μl of competent *E. coli* DH5αF' cells and plated on 2YT plates containing ampicillin, Xgal and IPTG. After 16 h incubation at 37° C., whites colonies are picked and miniscreened using PstI and EcoRI digests to confirm the presence of the correct inserts. The GAPFLyHIR expression cassette is transcribed in the opposite direction to ampR in pFBY99 and in the same direction as ampR in pFBY99R.

pFBY96, pFBY96R, pFBY97, pFBY97R, pFBY98, pFBY98R, pFBY99 and pFBY99R form a set of disintegration vectors which when transformed into *S. cerevisiae* yield by recombination plasmids which can be grouped into pairs. Both members of each pair being almost exactly the same as each other merely differing in the relative position of a 136 bp sequence that contains a FRT site. Thus pFBY96 and pFBY99 form a pair, pFBY96 being assymmetric and pFBY99 being symmetric. Likewise, the symmetric pFBY96R forms a pair with the asymmetric pFBY99R, the symmetric pFBY97 with the asymmetric pFBY98 and the symmetric pFBY97R with the asymmetric pFBY98R.

EXAMPLE 24

Testing of the stability of symmetric versus assymmetric plasmids in *S. cerevisiae*

All four pFBY12 plasmids, all 8 pFBY13 plasmids, and all pFBY96's, pFBY97's, pFBY98's and pFBY99's are transformed into *S. cerevisiae* strain H449 (leu2, ura3) by selection on supplemented YNB for complementation of leu2 or ura3 auxotrophies.

At least 5 independent *S. cerevisiae* transformants are streaked out for single colonies on YNB plus leucine. After 2 days at 30° C. a single colony from each transformant is picked into 2.5 ml of YPD(HE16) in a 10 ml tube and grown for 24 h at 30° C. at 200 rpm.

The number of cells are estimated from the OD or by directly counting with a hemocytometer and each culture is diluted appropriately to yield 1000 colonies per ml. 100 μl aliquots of each sample are plated onto three YPD plates.

After 2 days at 30° C. these are replicated using filter paper onto appropriately supplemented YNB plus leucine and after a further 2 days incubation at 30° C. the number of colonies that contained the plasmid and the number of colonies that no longer contain the plasmid are counted.

The stability of the plasmid is expressed as the percent of the cells that lose the plasmid after 24 h in nonselective YPD media.

These experiments are repeated with the *S. cerevisiae* strain AB110 (leu2 ura3 his4) in an identical manner except that histidine is included in all YNB media.

The data are given in the following tables.

TABLE 1

Stability of symmetric and asymmetric two micron-like hybrid vectors in transformed *S. cerevisiae* cells

| | | % plasmid loss | |
|---|---|---|---|
| Plasmid | r/l | H449 | AB110 |
| pFBY12 | 1.17 | nd | 30 |
| pFBY12P | 3.28 | nd | 63 |
| pFBY12R | 1.17 | nd | 3.5 |
| pFBY12PR | 3.28 | nd | 6.3 |
| pFBY13 | 1.31 | 5.3 | 15 |
| pFBY13P | 3.65 | 5.8 | 28 |
| PFBY13R | 1.31 | 6.8 | 28 |
| pFBY13PR | 3.65 | nd | 43 |
| pFBY13rev | 1.31 | 1.8 | 3 |
| pFBY13Prev | 3.65 | 5.1 | 11 |
| pFBY13revR | 1.31 | 1.8 | 8 |
| pFBY13revR | 3.65 | 4.7 | 30 | r/l is the ratio of the lengths of the regions between the two invertedly repeated FRT sites of the plasmids.

The plasmids in Table 1 are arranged in pairs that differ only in the position of the deletion of the XbaI and surrounding region in the FRT site. This alteration in stabilities between different plasmids and different strains is not explained fully at this stage and the plasmid stabilities that we observe here are not very good compared to the stability of native two micron plasmid of *S. cerevisiae* which is spontaneously lost extremely rarely ($10^{-4}$ per cell per generation). It is clear that when comparing two otherwise identical plasmids that differ only in the relative position of the active FRT sites that the more symmetric constructs are consistently more stable than the assymetric ones over a wide range of absolute stabilities.

One factor influencing this instability of hybrid two micron plasmids is the presence of bacterial sequences in the yeast plasmid. This is already published in the PCT patent application WO88/08027 and is confirmed by the results shown in Table 2:

TABLE 2

| Plasmid | r/l | % plasmid loss *S. cerevisiae* cells (AB110) |
|---|---|---|
| pFBY8R | 2.31 | 0.6 |
| pFBY12R | 1.17 | 3.5 |
| pFBY12PR | 3.28 | 6.3 | pFBY8R is identical to pFBY12R and pFBY12PR except it has all three active FRT sites and hence deletes the bacterial derived pTZ18R sequences when propagated in *S. cerevisiae*. Although pFBY8R is not as symmetric as pFBY12R it is more stable, presumably because it does not contain the pUC sequences. The flipping and deletion of bacterial sequences of all these plasmids are confirmed by Southern blot hybridization of *S. cerevisiae* genomic DNA extracted from these transformants.

To assess the stability of vectors that are both symmetric and lack pUC sequences a set of plasmids pFBY96, pFBY97, pFBY98, pFBY99 and their R derivatives are constructed. These are transformed into *S. cerevisiae* H449 and their stabilities are compared. The results are shown in Table 3.

The plasmids in Table 3 are arranged in pairs that differ only in the position of the 136 bp FRT site. Again it is clear that the more symmetric plasmids are more stable than the corresponding assymmetric derivatives.

TABLE 3

| Plasmid | r/l | % plasmid loss |
|---|---|---|
| pFBY96 | 1.8 | 3.2 |
| pFBY99 | 1.02 | 1.3 |
| pFBY96R | 1.8 | 10.2 |
| pFBY99R | 1.02 | 2.9 |
| pFBY97 | 1.8 | 2.9 |
| pFBY98 | 1.02 | 0.7 |
| pFBY97R | 1.8 | 7.3 |
| pFBY98R | 1.02 | 1.8 |

EXAMPLE 25

Hirudin Yields from Symmetric Plasmids

In order to assess the usefulness of these plasmids as vectors for the production of heterologous proteins pFBY27 and pFBY27R, and pFBY79 and pFBY79R are constructed. Theses plasmids are designed to be symmetric and not to contain bacterial derived pUC sequences when propagated in *S. cerevisiae*.

pFBY27 and pFBY27R contain the URA3 marker and a hirudin expression cassette that is the same size as URA3 to give a r/l ratio of 1.02. When assessed for stability in H449 by growing in non selective media for 24 h the %age of plasmid free cells is less than 0.5.

pFBY79 and pFBY79R contain a 2 kb LEU2 insert in one half of the plasmid and URA3 and a hirudin expression cassette in the other to give a r/l ratio of 0.87 and a 24 hr stability in H449 of 0.2 plasmid loss.

These plasmids transformed into H449 are grown in shake flasks and assayed for hirudin. The transformants are streaked for single colonies on YNB+glucose+leucine solid medium. A single colony is inoculated into 50 ml of minimal medium (8.4 g L Difco Yeast Nitrogen Base without amino acids, 10 g L-asparagine, 1 g L-histidine, 40 mg/l L-leucine, 2% glucose) in 250 ml flasks and grown at 180 rpm and 30° C. for 72 h. A sample is removed for assay. Then the culture is diluted 1:10 into YPD medium and incubated further at 180 rpm and 30° C. Samples being removed every 24 h. Supernatants are obtained from the samples by centrifuging at 3000 g for 5 min and used directly for assays.

Hirudin is assayed by its concentration dependent inhibition of thrombin. Thrombin activity is followed by the release of p-nitro-aniline from the chromogenic peptide substrate tosyl-glycyl-prolyl-arginine-4-nitranilide acetate (Chromozym TH, Boehringer Mannheim, FRG). The buffer used is 0.2M Tris. HCl pH 7.5, 1M NaCl, 0.01% bovine serum albumin. All Assays are performed in microtiter plates. Each well contains 50 µl of human thrombin (Novabiochem, Läufelfingen, Switzerland). The reaction is started by the addition of 150 µl of substrate (333 µg/ml). The plates are incubated for 2 h at 37° C. and the optical density is read at 405 nm in a Dynatech MR 600 microliter plate reader. Thrombin is used at a concentration to reach 0.8

OD$_{405}$ in uninhibited control wells. All optical densities are corrected for the OD$_{405}$ that is determined before the start of the incubation. Unknown hirudin concentrations are calculated from a standard curve obtained with six hirudin concentrations. All measurements are made at least in duplicates. The assay is sensitive enough to allow a 100-fold dilution before assaying the samples.

The results clearly show that the symmetric plasmids are not only stable but produce upto 25% more hirudin than the corresponding asymmetric plasmids.

EXAMPLE 26

IGF-I Yields from Symmetric Plasmids

For IGF-I expression using these more stable symmetric plasmids pFBY66 and pFBY66R, and pFBY79IGF and pFBY79IGFR are constructed. Theses plasmids are designed to be symmetric and not to contain bacterial derived pUC sequences when propagated in *S. cerevisiae*.

pFBY66 and pFBY66R contain the URA3 marker and an IGF-I expression cassette that is the same size as URA3 to give a r/l ratio of 1.15. When assessed for stability in AB110 by growing in non selective media for 24 h the %age of plasmid free cells is 3.6 for pFBY66 and 0.6 for pFBY66R compared to 37% for an assymetric plasmid pDP34A-GAPDH-AFL-IGF1-AFT in the same strain.

These plasmids transformed into AB 110 are grown under standard conditions in shake flasks and assayed for IGF-I.

A rich medium containing 6.5 g/l yeast extract, 4.5 g/l casamino acids and 30 g/l glucose is used as non-selective preculture medium. The main culture is done in a uracil selective medium containing 1.7 g/l yeast nitrogen base supplemented with 30 g/l glucose, 8.5 g/l casamino acids and the required amino acids. Usually *S. cerevisiae* cells are grown at 28° C. and 180 rpm overnight in the preculture medium and in the main culture for up to 72 h in a volume of 50 ml.

The IGF-I concentrations in the culture media are determined by reversed phase HPLC. 10 ml sample of the *S. cerevisiae* culture is centrifuged at 3 000 g for 5 min. The supernatant is removed and adjusted to pH 3.0 with 15% H$_2$SO$_4$. 50 µl of this adjusted culture media are separated by HPLC on a C$_{18}$ column (Nucleosil C$_{18}$, 4×125 mm, 30 nm, spherical 5 gm, Macherey-Nagel, Düren, FRG). The elution is performed at room temperature using a linear gradient of buffer A (0.1% v,v trifluoroacetic acid) with buffer B (80% v,v acetonitrile containing 0.075% TFA with 20% v,v buffer A) at pH 2. The buffer B content is increased from 10% to 31% in 1 min, kept isocratic for 8 min at a flow rate of 1.5 ml/min. The eluate is monitored by UV detection at 214 nm. The IGF-I content is obtained by comparing the protein peak to the peak area of a known standard sample.

The symmetric stable plasmids pFBY66 and 66R produce twice as much IGF-I than the corresponding asymmetric plasmids.

Deposition of Microorganisms

*E. coli* DH5αF' transformed with following plasmids were deposited under the Budapest Treaty on Dec. 14, 1990 with the Deutsche Sammlung von Mikroorganismen und Zellkulturen, Mascheroder Weg 1b, D-3300 Braunschweig:

| Plasmid | Deposition No. |
|---------|----------------|
| pFBY2   | DSM 6271       |
| pFBY4   | DSM 6272       |
| pFBY5   | DSM 6273       |
| pFBY7   | DSM 6274       |
| pFBY29  | DSM 6275       |
| pFBY65  | DSM 6276       |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GGTTTTTGA AAGTGCGAGA TCTTCTTCAG AGCGCTTTTG G                                    4 1
```

I claim:

1. A manufactured circular yeast two micron-like plasmid comprising two invertedly repeated FRT sites, functional FLP, REP1, REP2 and D open reading frames and an expression cassette which codes for the production of a heterologous protein in a yeast cell, wherein the two regions between invertedly repeated FRT sites of the circular form of said plasmid have a ratio in length of from about 1:1 to about 5:4.

2. A manufactured yeast two micron-like plasmid according to claim 1 which contains only two FRT sites.

3. A manufactured yeast two micron-like plasmid according to claim 1 which is a two micron-like disintegration vector which gives rise to a two micron-like hybrid vector which contains two invertedly repeated FRT sites in the yeast cell transformed therewith.

4. A manufactured yeast two micron-like plasmid according to claim 2 which does not contain bacterial DNA sequences.

5. A manufactured yeast two micron-like plasmid according to claim 1 which is derived from the *S. cerevisiae* two micron plasmid.

6. A manufactured yeast two micron-like plasmid according to claim 1 which contains only two invertedly repeated FRT sites.

7. A manufactured yeast two micron-like plasmid according to claim 1 derived from the plasmids pSB1 or pSB2 from *Zygosaccharomyces bailii*, plasmid pSR2 from *Z. rouxii*, pSB3 from *Z. bisporus*, pSM1 from *Z. fermentati*, pKD1 from *Kluyveromyces drosophilarum* or the two micron plasmid of *S. cerevisiae*.

8. A manufactured yeast two micron-like plasmid according to claim 1 in which one of the two regions is up to about 20% larger than the remaining region.

9. A manufactured yeast two micron-like plasmid according to claim 1 comprising a heterologous structural gene derived from a virus, a prokaryotic cell or a eukaryotic cell.

10. A manufactured yeast two micron-like plasmid according to claim 9 in which the structural gene is coding for a human α-interferon or hybrid interferon, human tissue plasminogen activator (t-PA), hepatitis B virus surface antigen (HBVsAg), insulin-like growth factor I and II, eglin C or desulfatohirudin.

11. A manufactured yeast two micron-like plasmid according to claim 10 in which the structural gene is coding for hybrid interferon BDBB.

12. A manufactured yeast two micron-like plasmid according to claim 10 in which the structural gene is coding for desulfatohirudin.

13. A host transformed with a manufactured yeast two micron-like plasmid according to claim 1.

14. A transformed host according to claim 13 which is *E. coli* transformed with pFBY27, pFBY27R, pFBY27rev, pFBY27revR, pFBY66, pFBY66R, pFBY98R, pFBY98R, pFBY99, or pFBY99R.

15. A transformed host according to claim 13 which is *S. cerevisiae* transformed with pFBY27, pFBY27R, pFBY27rev, pFBY27revR, pFBY66, pFBY66R, pFBY98, pFBY98R, pFBY99, pFBY99R, pFBY12, pFBY12R, pFBY13, pFBY13R, pFBY13rev, or pFBY13revR.

16. A manufactured circular yeast two micron-like plasmid comprising functional FLP, REP 1, REP 2 and D open reading frames, having a first and second region between invertedly repeated FRT sites, said plasmid further comprising:
(1) an expression cassette which codes for the product of a heterologous protein in a yeast cell inserted into said first region; and
(2) a DNA sequence inserted into said second region, wherein the length of the DNA sequence in said second region is such that said first region and said second region have a ratio in length of from about 1:1 to about 5:4.

17. A manufactured yeast two micron-like plasmid according to claim 16 which is derived from the *S. cerevisiae* two micron plasmid.

18. A manufactured yeast two micron-like plasmid according to claim 1 derived from the two micron plasmid of *S. cerevisiae*.

19. A host transformed with a manufactured yeast two micron-like plasmid according to claim 16.

20. A transformed host according to claim 19 which is *E. coli* transformed with pFBY27, pFBY27R, pFBY27rev, pFBY27revR, pFBY66, pFBY66R, pFBY97R, pFBY99, or pFBY99R.

21. A transformed host according to claim 19 which is *S. cerevisiae* transformed with pFBY27, pFBY27R, pSBY27rev, pFBY27revR, pFBY66, pFBY66R, pFBY98, pFBY98R, pFBY99, pFBY99R, pFBY12, pFBY12R, pFBY13, pFBY13R, pFBY13rev, or pFBY13revR.

22. A manufactured yeast two micron-like plasmid according to claim 16 in which the first region is up to about 20% larger than the second region.

23. A manufactured yeast two micron-like plasmid according to claim 22 in which the first region is up to about 15% larger than the second region.

24. A manufactured yeast two micron-like plasmid according to claim 23 in which the first region is up to about 10% larger than the second region.

25. A manufactured yeast two micron-like plasmid according to claim 24 in which the first region is up to about 5% larger than the second region.

26. A manufactured yeast two micron-like plasmid according to claim 16 wherein said heterologous structural gene is derived from a virus, a prokaryotic cell or a eukaryotic cell.

27. A manufactured yeast two micron-like plasmid according to claim 26 in which the structural gene encodes an enzyme which can be used for the production of nutrients or for performing enzymatic reactions, or a polypeptide which is useful as nutrient or for the treatment of human or animal diseases or for the prevention thereof.

28. A manufactured yeast two micron-like plasmid according to claim 27 in which the structural gene is coding for a human α-interferon or hybrid interferon, human tissue plasminogen activator (t-PA), hepatitis B virus surface antigen (HBVsAg), insulin-like growth factor I and II, eglin C or desulfatohirudin.

29. A manufactured yeast two micron-like plasmid according to claim 28 in which the structural gene is coding for hybrid interferon BDBB.

30. A manufactured yeast two micron-like plasmid according to claim 28 in which the structural gene is coding for desulfatohirudin.

31. A manufactured yeast two micron-like plasmid according to claim 16 selected from the group of vectors consisting of pFBY12, pFBY12R, pFBY13, pFBY13R, pFBY13rev and pFBY13revR.

32. A manufactured yeast two micron-like plasmid according to claim 16 selected from the group of vectors consisting of pFBY27, pFBY27R, pFBY27rev, pFBY27revR, pFBY66, pFBY66R, pFBY98, pFBY98R, pFBY99, and pFBY99R.

33. A manufactured yeast two micron-like plasmid according to claim 16 derived from the plasmids pSB1 or pSB2 from *Zygosaccharomyces bailii*, plasmid pSR2 from *Z. rouxii*, pSB3 from *Z. bisporus*, pSM1 from *Z. fermentati*, pKD1 from *Kluyveromyces drosophilarum* or the two micron plasmid of *S. cerevisiae*.

* * * * *